(12) United States Patent
Zhang et al.

(10) Patent No.: US 8,483,813 B2
(45) Date of Patent: Jul. 9, 2013

(54) SYSTEM AND METHOD FOR ESTABLISHING EPISODE PROFILES OF DETECTED TACHYCARDIA EPISODES

(75) Inventors: Xusheng Zhang, Shoreview, MN (US); Robert W. Stadler, Shoreview, MN (US); Douglas A. Hettrick, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 379 days.

(21) Appl. No.: 12/826,916

(22) Filed: Jun. 30, 2010

(65) Prior Publication Data
US 2012/0004566 A1    Jan. 5, 2012

(51) Int. Cl.
*A61B 5/0452* (2006.01)

(52) U.S. Cl.
USPC .......................................... 600/515

(58) Field of Classification Search
USPC ........................................... 600/515; 607/14
See application file for complete search history.

(56) References Cited

U.S. PATENT DOCUMENTS

| 5,271,411 | A | 12/1993 | Ripley |
| 6,266,554 | B1 | 7/2001 | Hsu |
| 6,301,503 | B1 | 10/2001 | Hsu |
| 6,400,986 | B1 | 6/2002 | Sun |
| 6,449,504 | B1 | 9/2002 | Conley |
| 6,922,585 | B2 | 7/2005 | Zhou |
| 7,123,954 | B2 | 10/2006 | Narayan |
| 2004/0215273 | A1 | 10/2004 | van Bolhuis |
| 2005/0137485 | A1 | 6/2005 | Cao |
| 2005/0256413 | A1 | 11/2005 | Astrom |
| 2007/0142736 | A1* | 6/2007 | Cazares et al. ................ 600/515 |
| 2007/0149890 | A1* | 6/2007 | Li et al. ......................... 600/515 |
| 2007/0239043 | A1 | 10/2007 | Patel |
| 2008/0071182 | A1 | 3/2008 | Cezares |
| 2008/0125824 | A1 | 5/2008 | Sauer |

OTHER PUBLICATIONS (PCT/US2011/042551) PCT Notification of Transmittal of the International Search Report and the Written Opinion of the International Searching Authority.

* cited by examiner

*Primary Examiner* — Eric D. Bertram
(74) *Attorney, Agent, or Firm* — Michael C. Soldner

(57) ABSTRACT

A medical device and associated method sense a cardiac signal and initiate an arrhythmia episode detection process in response to the cardiac signal by enabling an arrhythmia detection counter to be adjusted during the detection process. Data is accumulated relating to cardiac events during the detection process. An arrhythmia episode profile is established using the accumulated data. The accumulated data includes a pattern of the adjustment of the detection counter during the detection process.

26 Claims, 9 Drawing Sheets

SYSTEM AND METHOD FOR ESTABLISHING EPISODE PROFILES OF DETECTED TACHYCARDIA EPISODES

TECHNICAL FIELD

The present disclosure relates generally to implantable medical devices and, in particular, to a method and apparatus for establishing episode profiles for tachycardia episodes.

BACKGROUND

A typical implantable cardioverter defibrillator (ICD) has the capability of providing a variety of anti-tachycardia pacing (ATP) regimens as well as cardioversion/defibrillation shock therapy. Normally, arrhythmia therapies are applied according to a pre-programmed sequence of less aggressive to more aggressive therapies depending on the type of arrhythmia detected. Typically, termination of an arrhythmia is confirmed by a return to either a demand-paced rhythm or a sinus rhythm in which successive spontaneous R-waves are separated by at least a defined interval. When ATP attempts fail to terminate the tachycardia, high-voltage cardioversion shocks may be delivered. Since shocks can be painful to the patient and consume relatively greater battery energy than pacing pulses, it is desirable to avoid the need to deliver shocks by successfully terminating the tachycardia using less aggressive pacing therapies.

The success of a tachycardia therapy depends in part on the accuracy of the tachycardia detection. In some cases, a tachycardia originating in the atria, i.e. a supraventricular tachycardia (SVT), is difficult to distinguish from a tachycardia originating in the ventricles, i.e. a ventricular tachycardia (VT). For example, both the atrial chambers and the ventricular chambers may exhibit a similar tachycardia cycle length when an SVT is conducted to the ventricles or when a VT is conducted retrograde to the atria. Accordingly, accurate classification of a detected tachycardia as VT or SVT is needed in order to properly determine when a therapy is necessary.

Once a need for therapy is determined, it is desirable to select the most effective therapy for terminating a detected tachycardia. Currently available ICDs detect and treat an arrhythmia episode as a new episode independently of any previous arrhythmia history. In some cases, a patient may experience repeated episodes of a tachycardia rhythm that is electrophysiologically similar. It is desirable to select a therapy that is the most effective and least aggressive in terminating the tachycardia on the first therapy attempt. As such, it is desirable to know if a particular tachycardia rhythm, either atrial or ventricular, has occurred in the past and what the past therapy success rate has been.

DETAILED DESCRIPTION

Figure 1:
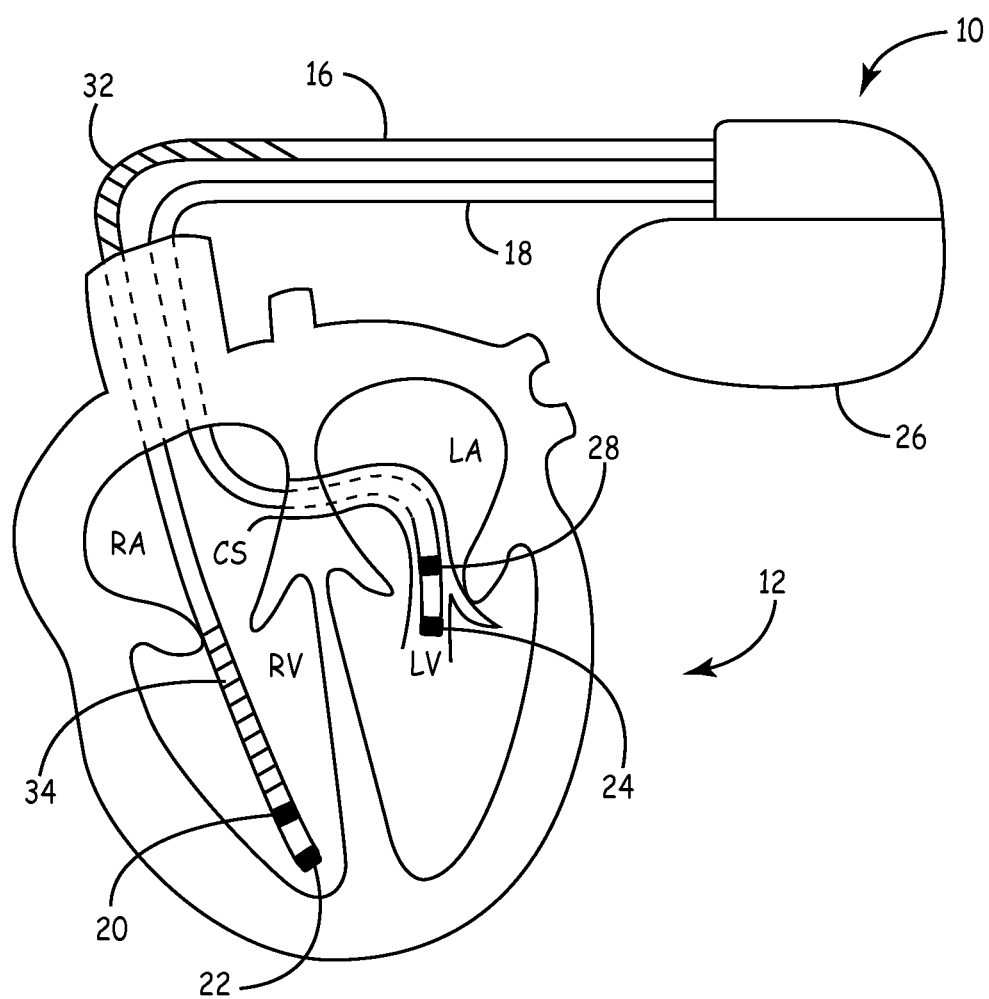
FIG. 1 is a schematic representation of an implantable medical device (IMD).

In the following description, references are made to illustrative embodiments. It is understood that other embodiments may be utilized without departing from the scope of the disclosure. In some instances, for purposes of clarity, identical reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic representation of an implantable medical device (IMD) 10. While IMD 10 is embodied as an ICD in FIG. 1, methods described herein, however, should not be interpreted as being limited to any particular implantable medical device or any particular cardiac medical device. Rather, embodiments may include any cardiac medical device so long as the device utilizes a plurality of electrodes or other sensors for monitoring the cardiac rhythm of a patient.

In FIG. 1, the right atrium (RA), left atrium (LA), right ventricle (RV), left ventricle (LV), and the coronary sinus (CS), extending from the opening in the right atrium to form the great cardiac vein, are shown schematically in heart 12. Two transvenous leads 16 and 18 connect IMD 10 with the RV and the LV, respectively. Each lead includes at least one electrical conductor and pace/sense electrode. The electrodes are capable of sensing cardiac EGM signals, also referred to as "cardiac signals", and delivering electrical pacing pulses to the cardiac tissue. For example, leads 16 and 18 are respectively connected to pace/sense electrodes 20, 22, and 24, 28. In addition, a housing electrode 26 can be formed as part of the outer surface of the housing of the device 10. The pace/sense electrodes 20, 22, and 24, 28 and housing electrode 26 can be selectively employed to provide a number of unipolar and bipolar pace/sense electrode combinations for pacing and sensing functions. The depicted positions in or about the right and left heart chambers are merely illustrative. Moreover, other leads and pace/sense electrodes can be used instead of, or in combination with, any one or more of the depicted leads and electrodes.

Typically, in pacing systems of the type illustrated in FIG. 1, the electrodes designated herein as "pace/sense" electrodes are used for both pacing and sensing functions. In certain embodiments, these electrodes can be used exclusively as pace or sense electrodes in programmed or default combinations for sensing cardiac signals and delivering pace pulses. The leads and electrodes described can be employed to record cardiac signals. The recorded data can be periodically transmitted to a programmer or other external device enabled for telemetric communication with the IMD 10.

An RV coil electrode 34 and a superior vena cava (SVC) coil electrode 32 are also shown as being coupled to a portion of RV lead 16. Coil electrodes can additionally or alternatively be coupled to portions CS lead 18. The coil electrodes 32 and 34, or other similar electrode types, can be electrically coupled to high voltage circuitry for delivering high voltage cardioversion/defibrillation shock pulses.

Electrodes shown in FIG. 1 can be disposed in a variety of locations in, around, and on the heart and are not limited to the locations shown. ICDs and pacemakers typically use a ventricular EGM signal for sensing ventricular events (R-waves) for determining a need for pacing and for detecting a RR intervals meeting tachycardia detection criteria. An EGM sensing vector may be a unipolar or bipolar sensing vector using one or two electrodes, respectively, placed in or on the ventricular heart chambers. Embodiments described herein are not limited to use with intracardiac or transvenous leads as shown in FIG. 1. Subcutaneously implanted electrodes or even external electrode systems may be used.

Furthermore, other transvenous lead and electrode systems may be substituted for the system shown in FIG. 1. A detection algorithm may or may not use electrodes for sensing atrial signals for detecting and discriminating treatable rhythms. IMD 10 is shown coupled only to ventricular leads 16 and 18 but implementation of a selected detection algorithm is not limited to systems employing only ventricular leads. In other embodiments, dual chamber or multi-chamber systems may be used which include atrial leads used to position electrodes in, on or around the atrial chambers. Systems that employ atrial leads without the use of ventricular leads may also be used depending on the detection algorithm(s) implemented for detecting arrhythmia episodes.

Figure 2:
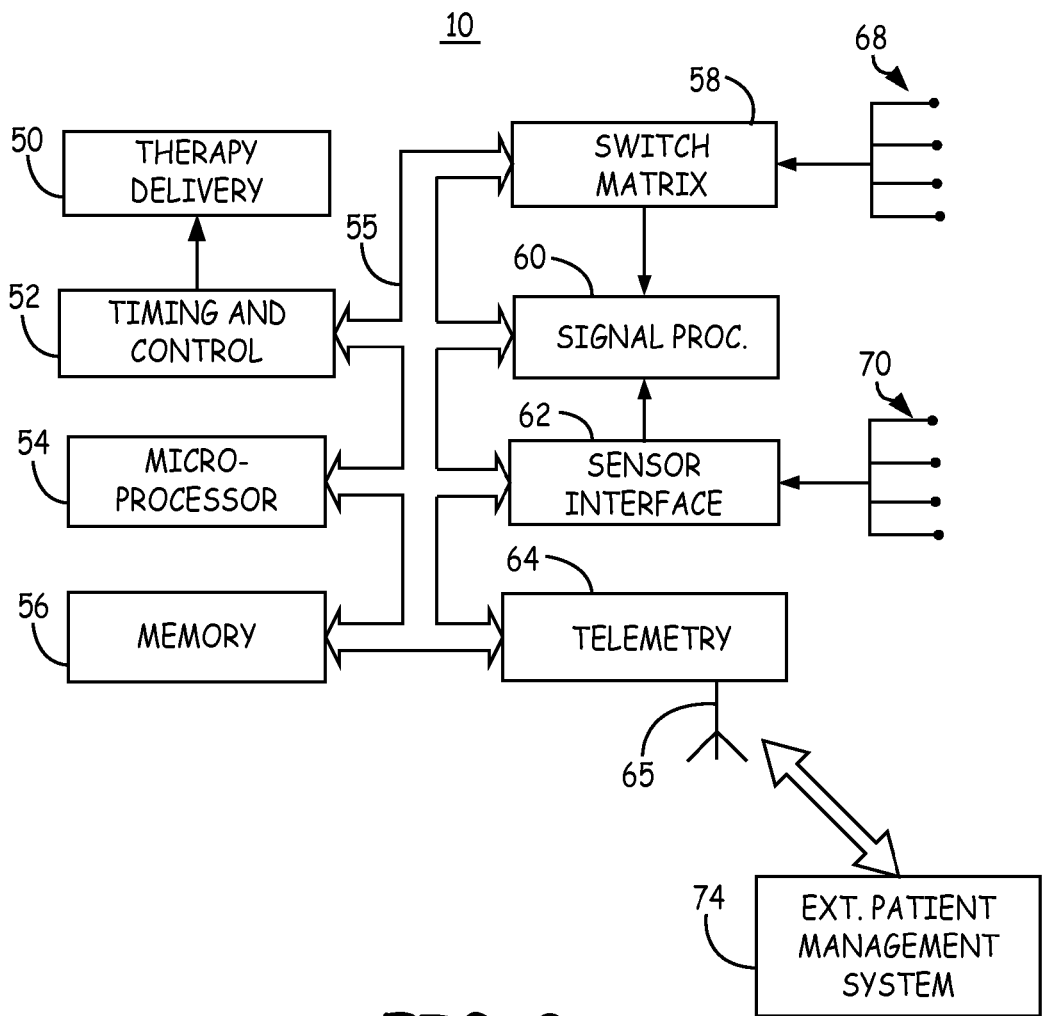
FIG. 2 is a functional block diagram of the IMD shown in FIG. 1 according to one embodiment.

FIG. 2 is a functional block diagram of the IMD 10 shown in FIG. 1 according to one embodiment. IMD 10 generally includes timing and control circuitry 52 and a controller that may be embodied as a microprocessor 54 or a digital state machine for timing sensing and therapy delivery functions in accordance with a programmed operating mode. Microprocessor 54 and associated memory 56 are coupled to the various components of IMD 10 via a data/address bus 55. IMD 10 includes therapy delivery module 50 for delivering electrical stimulation pulses to a patient's heart including cardiac pacing pulses, arrhythmia pacing therapies such as anti-tachycardia pacing (ATP) and cardioversion/defibrillation shocks, under the control of timing and control 52 and microprocessor 54. Therapy delivery module 50 is typically coupled to two or more electrodes 68 via an optional switch matrix 58. Electrodes 68 correspond to the various electrodes shown in FIG. 1. An optional switch matrix 58 is used for selecting which electrodes and corresponding polarities are used for delivering electrical stimulation pulses.

Cardiac electrical signals are sensed for determining when an electrical stimulation therapy is needed and in controlling the timing of stimulation pulses. Electrodes used for sensing and electrodes used for stimulation may be selected via switch matrix 58. When used for sensing, cardiac signals received by electrodes 68 are coupled to signal processing circuitry 60 via switch matrix 58. Signal processor 60 includes sense amplifiers and may include other signal conditioning circuitry such as filters and an analog-to-digital converter. Cardiac electrical signals may then be used by microprocessor 54 for detecting physiological events, such as detecting and discriminating cardiac arrhythmias. Signal processing circuitry 60 includes cardiac event sensing circuitry for sensing ventricular events, e.g. R-waves and/or P-waves for use in determining event intervals and waveform morphology.

A tachycardia detection algorithm is implemented by the IMD controller (microprocessor 54) for detecting and discriminating arrhythmias. Sensed ventricular event intervals (RRIs) and R-wave morphology can be used in detecting and discriminating VT from SVT. A determination as to whether the heart rhythm is a treatable rhythm can be made based on ventricular EGM signals without requiring the use of atrial signals. In some embodiments, atrial signals may also be received and used in detecting and discriminating arrhythmias.

In response to detecting VT or VF, referred to inclusively hereafter as "VT", a therapy is delivered by therapy delivery module 50 under the control of timing and control 52. The therapy may be delivered according to a programmed menu of therapies. Arrhythmia therapies may include a menu of tiered therapies in which less aggressive ATP regimens are delivered first and, when not successful, a high voltage shock therapy is delivered. As will be described herein, an arrhythmia rhythm may be further distinguished based on a derived episode profile. The episode profile may be used in selecting a therapy in response to comparing the derived episode profile to historical episode profiles.

IMD 10 may additionally be coupled to one or more physiological sensors 70 carried by leads extending from IMD 10 or incorporated in or on the IMD housing. Signals from sensors 70 are received by a sensor interface 62 which provides sensor signals to signal processing circuitry 60. Sensor signals may be used by microprocessor 54 for detecting physiological events or conditions.

The operating system includes associated memory 56 for storing a variety of programmed parameter values that are used by microprocessor 54. The memory 56 may also be used for storing data compiled from sensed EGM or ECG signals and other sensed physiological signals and/or relating to device operating history for telemetry out on receipt of a retrieval or interrogation instruction. Parameters and tachycardia discrimination rules and algorithms may be stored in memory 56 and utilized by microprocessor 54. As described in detail herein, a history of episode profiles may be stored in memory and used in distinguishing between different types of arrhythmia episodes experienced by the patient.

IMD 10 further includes telemetry circuitry 64 and antenna 65. Programming commands or data are transmitted during uplink or downlink telemetry between ICD telemetry circuitry 64 and external telemetry circuitry included in a programmer or monitoring unit. A physician using an external interface (e.g. keyboard, mouse, touchscreen) may provide input via an external patient management system 74 in communication with the ICD, directly or indirectly. The patient management system 74 may include an IMD programmer, patient home monitor, computer, networked database or other external interactive patient management system components. A physician using the external patient management system 74 may provide input relating to an arrhythmia episode profile. The input may be used in combination with data obtained by the ICD to distinguish between episode profiles.

Figure 3:
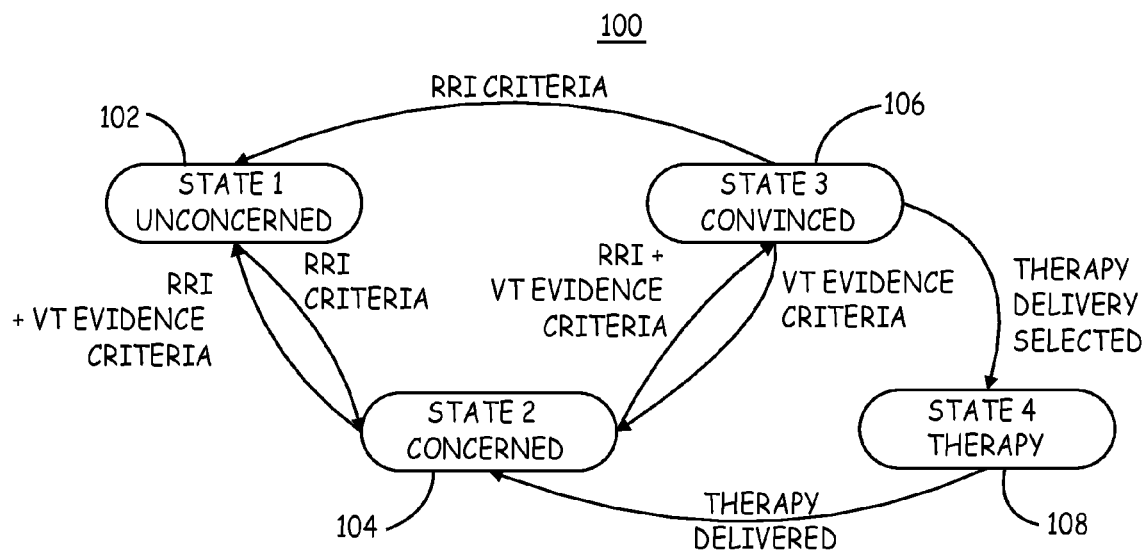
FIG. 3 is a state diagram of operating states included in a tachycardia detection and discrimination algorithm.

FIG. 3 is a state diagram 100 of operating states included in one embodiment of a tachycardia detection and discrimination algorithm that may be used in conjunction with establishing arrhythmia episode profiles. The tachycardia detection algorithm includes four operating states 102, 104, 106 and 108. State 1 102 is an unconcerned state in which RRI monitoring is occurring. An analysis of RRIs is performed to detect a sudden change in the heart rhythm. A sudden change may be a sudden change in heart rate (HR), i.e., a sudden change in the length of RRIs, or a sudden change in RRI variability, i.e., a sudden change in RRI differences.

A transition to State 2 104, the concerned state, occurs when either sudden change detection criteria or high heart rate criteria applied to measured RRIs are met in State 1 102.

A transition from State 1 to State 2 occurs based on RRI monitoring without performing QRS waveform morphology analysis. In order to enter State 2 104, an increase in HR has been detected in State 1 102 such that RRIs that are shorter than a detection lower limit interval have been measured.

State 2 104 is a "concerned state" because the HR is increased but the heart chamber that the fast ventricular rate is originating in may still be uncertain. Additional analysis is needed to discriminate between SVT and VT. During State 2, evidence of VT is accumulated on a beat-by-beat basis using morphology analysis of the ventricular EGM signals. A VT evidence counter is enabled in response to the initiating event of a sudden change being detected in State 1. The morphology analysis is used in State 2 in addition to the RRI analysis to determine if the rhythm is a "treatable" VT rhythm or "non-treatable" SVT rhythm when the detection algorithm is implemented in a single chamber, ventricular ICD.

Transition out of State 2, either back to State 1 (unconcerned) or forward to State 3 (convinced) can occur based on RRI data alone or a combination of RRI data and EGM signal morphology data. As such, in State 2 104, RRI monitoring continues and additional monitoring of EGM signal morphology is performed to accumulate evidence of VT, using a VT evidence counter that is adjusted on a beat-by-beat basis. If RRI criteria and VT evidence satisfies VT detection criteria, a transition to State 3 106 occurs. If RRI criteria and/or VT evidence no longer meet the criteria required to remain in State 2, a transition back to State 1 102 occurs.

Once State 3 106 is reached, VT is detected and a therapy selection process begins, e.g. according to a programmed menu of therapies. Since the onset of the therapy may be delayed due to capacitor charging, a programmed therapy delay, or other reasons, the IMD control system may remain in State 3 for an interval of time. RRI monitoring and morphology analysis performed in State 2 continues in State 3. As long as State 3 106 persists, the algorithm is "convinced" that the current rhythm is a treatable rhythm. As will be further described below, an episode profile may be established which includes determining a pattern of VT evidence accumulation that occurs beginning from initial entry into the "concerned" State 2 until the "convinced" State 3 is reached. The episode profile may further include information that is obtained during State 3 as well as during the therapy delivery State 4 108. Additionally, an episode profile may include data relating to events occurring in State 1 leading up to the transition to State 2.

A transition from State 3 106 directly to State 1 102 can occur if the RRI data indicates that the HR falls below a concerning rate, i.e. below the detection lower rate limit. A transition back to State 2 104 may occur if RRI data or morphology analysis no longer satisfy VT detection criteria but remain above a threshold for the concerned state. As such, an episode profile may be obtained over a period of time that includes more than one transition between State 3 and State 2.

A transition from State 3 106 to State 4 108 occurs once a therapy selection has been made and when a pending therapy is ready for delivery. For example, a therapy delay, capacitor charging or other time interval leading up to actual therapy onset expires and a transition to State 4 is made. Therapy is delivered in State 4. After therapy delivery, a transition back to state 2 104 occurs to continue monitoring the heart rhythm. The detection and discrimination algorithm remains in State 2 104 until reaching a decision to return to State 1 102 or to State 3 106 based on RRI criteria and morphology analysis.

Additional details regarding methods and algorithms performed in the various states shown in FIG. 3 are generally disclosed in U.S. Pat. Application No. 61/328,665, hereby incorporated herein by reference in its entirety. Another example of a state based detection algorithm that may be implemented in conjunction with the episode profiling described below is described in U.S. patent application Ser. No. 11/461,269, hereby incorporated herein by reference in its entirety.

Figure 4:
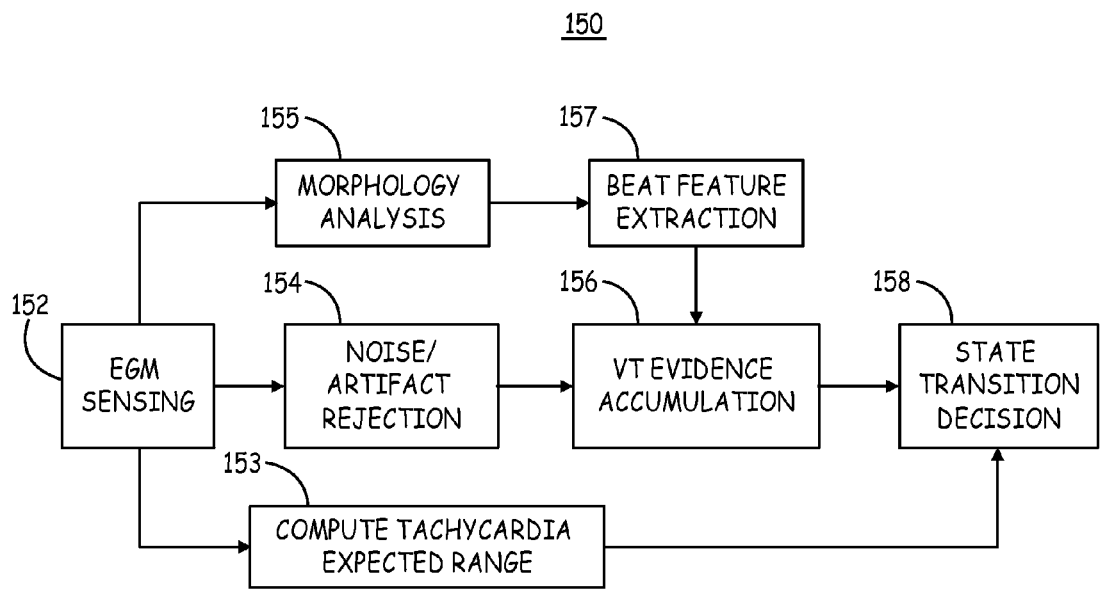
FIG. 4 is a flow chart of one embodiment of an arrhythmia detection algorithm that may be used in conjunction with the arrhythmia episode profiling methods described herein.

FIG. 4 is a flow chart 150 of one embodiment of an arrhythmia detection algorithm that may be used in conjunction with the arrhythmia episode profiling methods described herein. Flow chart 150 and other flow charts presented herein are intended to illustrate the functional operation of the device, and should not be construed as reflective of a specific form of software or hardware necessary to practice the methods described. It is believed that the particular form of software, firmware and/or hardware will be determined primarily by the particular system architecture employed in the device and by the particular detection and therapy delivery methodologies employed by the device. Providing software, firmware and/or hardware to accomplish the described functionality in the context of any modern medical device, given the disclosure herein, is within the abilities of one of skill in the art.

Methods described in conjunction with flow charts presented herein may be implemented in a computer-readable medium storing instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The tachycardia detection algorithm uses EGM signals sensed from at least one sensing vector at block 152. In one embodiment, two sensing vectors are used for performing tachycardia detection operations including computing a tachycardia expected RRI range at block 153, rejecting noise/artifact at block 154, performing an overall signal morphology analysis at block 155, and for extracting specific beat features at block 157 for additional analysis when needed. In one embodiment, two sensing vectors are selected to provide one near-field (NF) EGM signal and one far-field (FF) EGM signal.

At block 153, a tachycardia expected range is computed from one of the EGM signals, e.g. the NF EGM signal. The tachycardia expected range, represents an RRI range expected from the current, concerning rhythm.

At block 154, a noise/artifact rejection process is performed which analyzes each of the FF and NF EGM signals to determine the presence of noise or artifact that may corrupt the tachycardia discrimination algorithm. Each heart beat will be given a noise/artifact classification to exclude corrupted beats from contributing to the tachycardia discrimination methods. Various methods for detecting noise or artifact in the EGM signals may be used.

Each heart beat that is classified as a non-corrupted beat is analyzed morphologically at blocks 155 and 157 as needed. The results of an overall morphology analysis and specific beat feature analysis contribute in a cumulative manner on a beat-by-beat basis to a VT evidence metric at block 156. As described in detail in the above-incorporated '665 application, a VT evidence counter is adjusted beat-by-beat according to specific rules relating to an overall morphology analysis of a FF EGM signal and/or a NF EGM signal and/or specific beat features of the FF and/or NF EGM signals.

In some rhythms, changes in specific beat features as compared to a normal sinus rhythm beat, on either the FF or NF EGM signals, may have a higher tachycardia discrimination power than an overall morphology assessment of the same signal alone. As such, specific beat features are used to enhance the sensitivity and specificity of the tachycardia discrimination method.

At block 158, the tachycardia expected range and a VT evidence counter are used in a VT detection process to detect VT and advance to convinced State 3, or to make a determination to return to the unconcerned State 1. An expected RRI range stored from State 1 operations may be used in making a decision to return to State 1. If the VT evidence counter has reached a detection threshold, VT will be detected and a transition from the concerned State 2 to the convinced State 3 occurs. Criteria are defined to govern the transition between State 2 and State 3 and from State 2 back to State 1. The criteria may include requirements applied to results of the noise/artifact rejection analysis 154, VT evidence accumulation (block 156), the tachycardia expected range (block 153).

Figure 5:
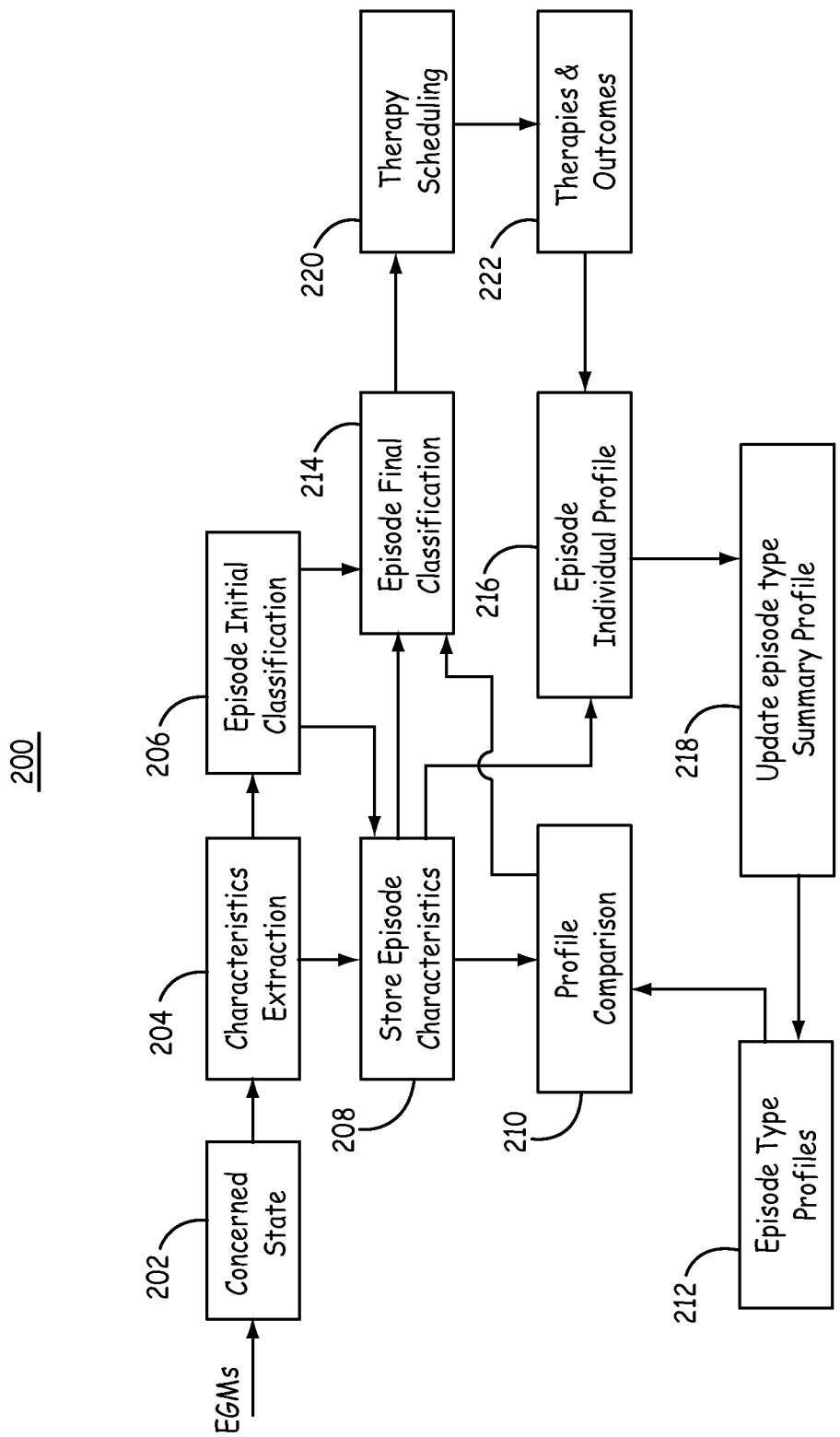
FIG. 5 is a flow chart of a method for establishing an episode profile of a detected tachycardia episode and using the episode profile in therapy selection.

FIG. 5 is a flow chart of a method for establishing an episode profile of a detected arrhythmia episode and for using the episode profile in therapy selection. Cardiac signals are provided as input to the concerned state 202. The concerned state is reached when a sudden change in the heart rhythm is detected, which may be a sudden change in heart rate or a sudden change in RRI variability. During the concerned state 202, episode characteristics are extracted at block 204 and stored at block 208. Extraction of episode characteristics occurs in addition to morphology score and various beat feature extraction that may be performed for accumulating evidence of VT on a beat-by-beat basis. Episode characteristics being extracted may include the morphology score and beat features that are being extracted for accumulating evidence of VT and may therefore not add significant processing power requirements to signal processing already being performed for VT detection.

Upon reaching detection criteria, the rhythm is classified based on the satisfied detection criteria at block 206. Transition to block 206 corresponds to a transition from a concerned state 202 to the convinced state 3 described above. The detection algorithm is convinced based on accumulated evidence that the current arrhythmia episode is VT. Episode characteristics leading up to the initial episode classification at block 206 are updated and stored upon the initial classification. The episode characteristics may be used in a final classification at block 214 which may differentiate different types of VT episodes that a patient may experience. For example, the initial episode classification may be a general VT detection, however, based on episode characteristics obtained relating to patterns or characteristics leading up to the VT detection, the final classification may separate different VT episodes that a patient experiences, which may be labeled generically as type 1, type 2 and so on, or more specifically based on episode profile parameters.

The final classification performed at block 214 may be used in scheduling a therapy, if needed, at block 220. Depending on the final classification, a more or less aggressive therapy may be scheduled. The therapy scheduling may take into account a history of previous therapy outcomes for the particular type of episode detected. In some cases, no therapy may be scheduled if the episode is classified as a type that is considered hemodynamically stable and/or has been observed to spontaneously terminate in the past patient history.

At block 222, the scheduled therapy is delivered. The therapy and its outcome are added to the episode profile at block 216 to complete the individual profile for the currently detected episode. It is recognized that the therapy scheduling and therapy delivery and outcome blocks 220 and 222 may be repeated one or more times depending on whether an attempted therapy is successful. If the episode is redetected after therapy delivery, another therapy is scheduled until the episode is no longer detected. While not explicitly shown in FIG. 5, it is to be understood that multiple therapies and associated outcomes may be added to the individual episode profile at block 216 when repeated therapies are required to terminate the arrhythmia.

The complete individual episode profile may be used to update a summary profile for the particular episode type at block 218. Different characteristics and aspects of a summary profile may be updated using the individual profile to provide a profile that is representative of a particular episode type. The summary profile may include ranges of values for various episode characteristics, a value or characteristic occurring with a highest rate of occurrence, average or mean values, etc. The individual episode profile record is used to update the historical episode profile at block 218 by merging episode characteristics for the individual profile with the historical profile. The merging may involve computing an average, which may be a weighted average in which less weight is given to the current individual profile than the stored historical profile.

Depending on the particular episode characteristic, various methods may be used to incorporate a new characteristic value from the individual profile into a summary profile. At block 212, the updated episode profile summary is stored with other historical episode profiles that the patient has experienced. If the patient has not experienced other types of episodes that are clinically distinguishable, then only a single episode type summary profile may be stored.

The stored summary profiles may be used in final classification of a detected episode at block 214. The episode characteristics stored at block 208 upon initially detecting and classifying an episode at block 206 may be compared to historical summary episode profiles at block 210. If the stored episode characteristics approximately match a historical profile, a final classification of the episode is determined at block 214 based on the match. A match result between current episode characteristics and stored summary profiles may be used alone or in conjunction with the individual episode characteristics stored at block 208 in classifying the episode at block 214.

Figure 6:
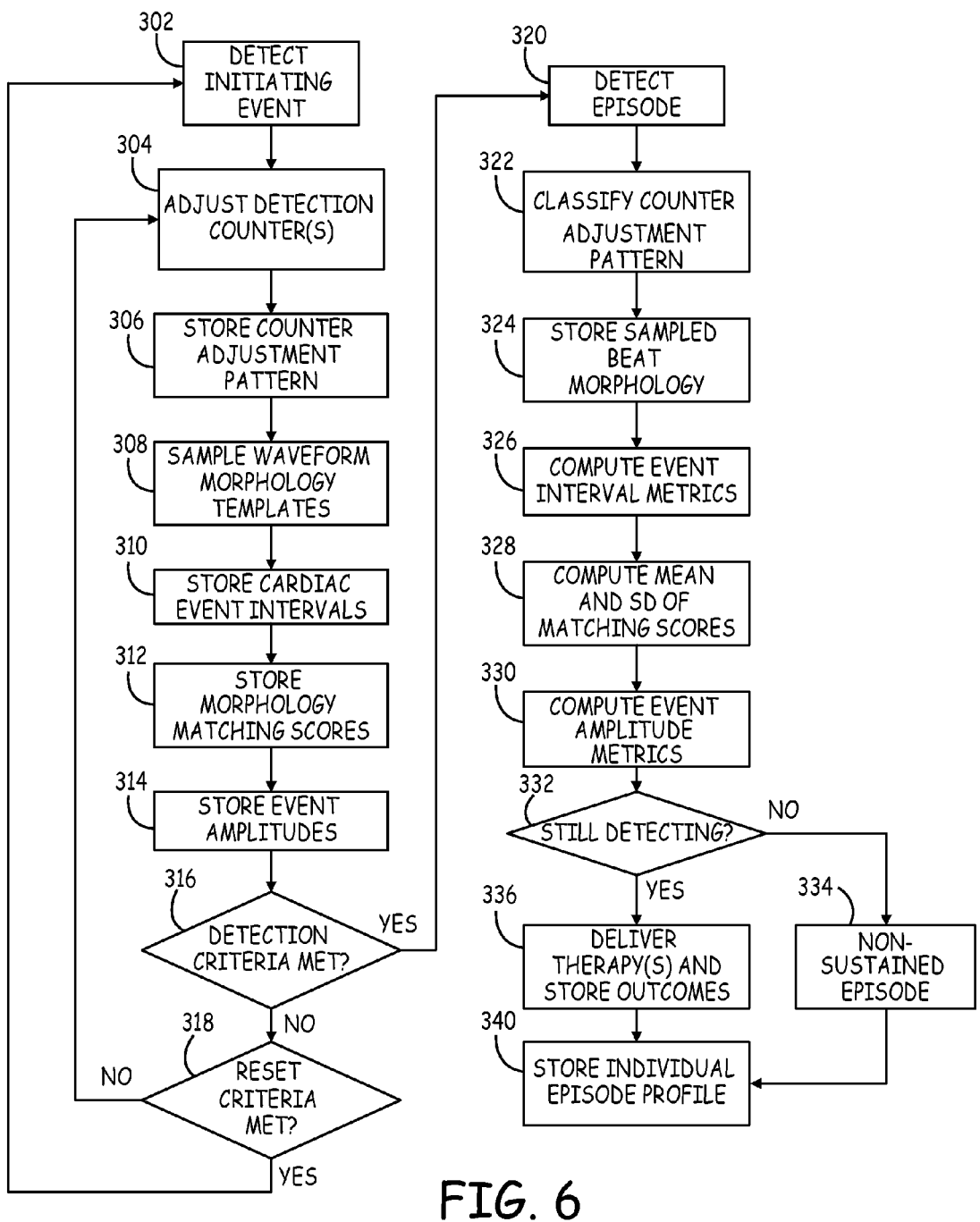
FIG. 6 is a flowchart of a method for extracting characteristics during episode detection and upon initial episode classification for use in establishing an episode profile.

FIG. 6 is a flowchart 300 of a method for extracting characteristics during episode detection and upon initial episode classification for use in establishing an episode profile. At block 302, an initiating event is detected which starts the adjustment of one or more arrhythmia detection counters. Arrhythmia detection counters may be adjusted on a beat-by-beat basis for detecting an arrhythmia episode or each time a cardiac sensed event or cardiac event interval meets criteria for detecting an arrhythmic beat. The methods described herein for establishing the episode profiles may be implemented in conjunction with various arrhythmia detection algorithms and are not limited to the detection algorithm described above in conjunction with FIGS. 3 and 4. As such, the initiating event and adjustment of detection counter(s) occurring at respective blocks 302 and 304 may vary between embodiments.

For example, a detection algorithm may define RR interval ranges corresponding to tachycardia and fibrillation detection intervals. When a required number of RRIs falls into a detection interval range, tachycardia or fibrillation is detected. Typical detection criteria might require at least 9 out of the most recent 12 RRIs are less than a tachycardia detection interval to detect tachycardia. A number of counters may be used to count the number of event intervals falling into respective detection interval ranges, e.g. slow VT, fast VT and VF interval ranges. In some embodiments, a combined count of VT and VF intervals is also counted. In this type of detection algorithm, an initiating event detected at block 302 might be the first VT or VF interval that causes a detection counter to advance from zero to one. The detection counter is adjusted thereafter at block 304 as additional VT or VF intervals are detected.

Another counter used for evaluating cardiac event morphology might become enabled upon reaching a threshold count of VT or VF intervals that triggers morphology analysis. The number of QRS waveforms having a morphology that corresponds to VT or VF may be counted. An initiating event at block 302 in this case may be the threshold number of detection intervals that results in a morphology analysis being invoked and a morphology-based counter used to confirm an arrhythmia detection.

Other algorithms may be used such as the beat-by-beat accumulation of VT evidence described in the above-incorporated '665 application. In this case a VT evidence counter is adjusted on each heartbeat in response to an analysis of a QRS morphology matching score and other specific beat features. In this embodiment, an initiating event at block 302 may be the detection of a sudden change or a high heart rate that causes a transition from State 1 (unconcerned) to State 2 (concerned) as described above.

Thus, the initiating event at block 302 may vary between embodiments and may be any initiating event that starts or enables one or more arrhythmia detection counter(s) to begin counting cardiac events, intervals or other features relied upon by an arrhythmia detection algorithm as an indication that an arrhythmia could be occurring. During the detection process, one or more detection counters are adjusted according to the rules or criteria established by the particular arrhythmia detection algorithm. During this detection process, data acquisition can already begin at blocks 306 through 314 for use in establishing an episode profile in case an arrhythmia episode is ultimately detected.

As one or more detection counters are adjusted at block 304, the pattern of adjustment is stored at block 306. The manner in which the counter adjustment pattern is stored will depend on the details of the detection algorithm. For example, the pattern may define how quickly (in time or total number of cardiac cycles) the counter increases to a detection threshold. The pattern may also define if the counter is continuously increased, e.g. on every successive cardiac cycle, intermittently increased, e.g. the counter is increased, remains at a current value for one or more cardiac cycles, then increases again, exhibits an increasing and decreasing pattern, or is reset to a zero value then begins to increase again within an established time interval or number of cardiac cycles.

Data stored at block 306 may initially include notations indicating an up, down or no change to the counter value for each cardiac cycle. Final pattern data will be stored upon reaching a detection threshold and detecting the arrhythmia episode as will be described further below.

At block 308, one or more EGM waveform morphology templates are sampled from the EGM signal during the time from initiating arrhythmia detection counter adjustment until episode detection is made. For example one or more QRS signal morphologies may be sampled and stored to provide a characteristic template to represent the rhythm occurring during the detection process.

At blocks 310 through 314, specific aspects of each cardiac cycle and/or cardiac event may be stored during the detection process, i.e. from the time a detection counter is first enabled to start counting arrhythmia events until a detection threshold is reached and an arrhythmia episode is detected. At block 310, each cardiac event interval is stored during the detection process. When morphology matching scores are computed, the scores are stored at block 312. The amplitude of each sensed event may be stored at block 314. It is recognized that features stored for establishing an episode profile are not limited to the features shown in the illustrative embodiment of FIG. 6. Among the other features of sensed events that may be stored are slew rate, event polarity, event width, and peak slope.

Referring to the illustrative detection algorithm described in conjunction with FIGS. 3 and 4, a VT evidence counter is adjusted at block 304 and the pattern of adjustment is stored at block 306. During State 2 operations, one or more waveform morphology templates are stored at block 308. According to the method described in the '615 application, each QRS waveform is compared to a known template to determine a matching score zone. At block 308, a waveform template stored as a sample template may be selected as a QRS signal that matches a particular zone, e.g. an SVT confident zone or a VT confident zone. A sample waveform template may be stored for each matching score zone that results from the waveform morphology analysis. For example, at least one sample template may be stored for waveforms falling into any of an SVT confident zone, an SVT gray zone, a VT gray zone and a VT confident zone, if they exist. At blocks 310 through 314, the morphology matching scores and/or any of the specific beat features described in the incorporated '615 application may be accumulated and stored for establishing an arrhythmia episode profile.

At decision block 316, a determination is made whether arrhythmia detection criteria are met. The current value of one or more detection counters may be compared to a respective detection threshold at block 316. If detection criteria are not met according to the implemented detection algorithm, a determination may be made at block 318 whether to clear acquired data for use in establishing an episode profile.

If a detection counter is initialized, i.e. increased from a zero value, and then is reset or returns to a zero value during the detection process before reaching a detection threshold count, episode profile data accumulated prior to the detection counter returning to a zero value may not correspond to an arrhythmia episode. If the counter remains at a zero for some time then begins to increase again, the events causing the counter to increase previously that did not result in an arrhythmia detection may not relate to a current arrhythmia episode that may be occurring. On the other hand, if the counter returns to zero briefly but then begins to increase again, the events may be related to a subsequently detected arrhythmia episode. As such, reset criteria may be defined in order to separate data that is acquired but does not ultimately lead directly to an arrhythmia detection and data that is acquired and does directly lead to an arrhythmia detection. For example, if a detection counter is at zero for a predetermined interval of time or number of cardiac cycles, the data acquired at blocks 306 through 314 may be cleared. In this case, the process returns to block 302 to wait for the next initiating event that causes the counter to begin increasing again. Furthermore, if there is a transition back to an unconcerned state 1 as described above, the accumulated episode profile data may be cleared at block 318. If the reset criteria are not met, the process returns to block 304 and data continues to be acquired, even if a counter has returned to zero or been reset to a zero value.

Alternatively, the data stored up to the point of reset criteria being met at block 318 may be stored as non-detected episode data. Non-detected episode data may be used to establish a non-detected episode profile that is stored with a date and time stamp, in a manner similar to a detected episode profile as will be described in detail below. Non-detected episode profile data may be useful to a clinician in evaluating precipitating events that lead up to an arrhythmia detection and optimizing detection parameters. For example, if a non-detected episode occurs within a short period of time prior to a detected episode, the non-detected episode may represent a precipitating rhythm or a non-sustained rhythm that was not detected.

If detection criteria are met at block 316, the arrhythmia episode is detected at block 320. The transition to block 320 may correspond to a transition to State 3 in the illustrative detection algorithm described above. A therapy may be scheduled accordingly. Upon detection, the episode profile is established using the data acquired during the detection process. At block 322, the counter adjustment pattern up to the point of detection is stored. The counter value at each cardiac cycle may be stored as the counter adjustment pattern at block 322 or other summary data may be stored. In one embodiment, the pattern may be stored as a series of flags or codes indicating the beat-to-beat change in the counter, which may be a series of digital flags indicating an upward, downward or no change for each beat.

Alternatively, summary metrics may be derived from the stored pattern. For example, a notation may be made indicating that the pattern was continuously increasing, intermittently increasing without decreasing, or intermittently increasing and decreasing. The total number of cardiac cycles or time duration that the detection counter took to reach a detection threshold after the initiating event may be stored as part of the counter adjustment pattern data. Other data may be used to quantify the counter adjustment pattern, such as on how many cardiac cycles did an increase occur, what was the average value of the increase of the counter each time it was incremented, how many times was the counter returned to a zero value during the detection process, etc.

At block 324, the sampled beat morphology template(s) are stored as a representative morphology for the detected episode. One or more templates may be stored, individually or averaged together to form a single representative template. From the morphology templates, a determination of whether the episode is monomorphic or polymorphic may be made and this classification may be stored as a part of the episode profile. A comparison of the morphology templates acquired near the beginning of the detection process and just prior or upon detection may also be performed to determine if a change in the rhythm is occurring, such as a deteriorating trend in the rhythm.

At block 326, metrics relating to the stored cardiac event intervals are computed and stored. Metrics relating to event intervals may include both rate and interval variability data. Event interval metrics may be computed using all or selected ones of the cardiac cycles from the initiating event leading up to episode detection and may include cycles preceding the initiating event and following episode detection. Metrics may include, but are not limited to, ventricular or atrial rate, interval variability, rate onset information, and atrial-ventricular association. An average rate may be determined along with a determination whether the rate is accelerating, decelerating or stable.

Metrics derived from the event interval data corresponding to event interval variability may include measurements of consecutive RR (or PP) interval differences and relative changes in the interval differences. Other data that may be stored for use in establishing an episode profile may include counter values corresponding to a low variability mode and a high variability mode of operation of a tachycardia detection algorithm for detecting a sudden change during the unconcerned State 1 operation. Detection of a sudden change in State 1 is the initiating event that enables counters used in a detection process in the concerned State 2. Low variability and high variability operation modes for detecting a sudden change and enabling a VT evidence counter are described in detail in the above-referenced '615 application. Briefly, during a low variability mode of operation, a sudden change in heart rate is detected as an initiating event that enables a process for accumulating evidence of a ventricular tachycardia in a VT evidence counter. During a high variability mode of operation, a sudden change in RR interval variability is detected as an initiating event that enables the accumulation of evidence of VT using the VT evidence counter. The values of any counters used in the low and high variability modes of operation may be stored for use in establishing an episode profile.

Details regarding detection of rate onset are described in U.S. patent application Ser. No. 12/430,301, hereby incorporated herein by reference in its entirety. Briefly, the variability of n most recent RRIs and the relative change between the sum of those n most recent RRIs and the preceding n RRIs are examined to detect tachycardia rate onset. When the variability is less than a variability threshold and the relative change is greater than a relative change threshold, the current beat is detected as the tachycardia rate onset beat. The beat detected as the tachycardia rate onset may be stored relative to the initiating event and/or the time of episode detection.

Data may also be stored relating to atrial-ventricular (AV) dissociation or association. The ratio (e.g. 1:1, 2:1) or pattern of atrial sensed events to ventricular sensed events may be stored. If atrial and ventricular events are not associated in any regular pattern or ratio, an indicator of AV dissociation may be stored.

At block 328 a mean and standard deviation of any morphology matching scores computed during the detection process may be calculated and stored. Alternatively a percentage of beats falling into different morphology matching score zones may be stored. Other summary data of morphology matching scores computed during the detection process, such as the range of matching scored obtained, may be stored.

At block 330, event amplitude metrics are calculated and stored. The event amplitudes stored during the detection process at block 314 may be used to compute a maximum, minimum, mean and standard deviation, or other summary metrics of the event amplitude metrics. A percentage of event amplitudes just meeting the sensing threshold or within a predetermined range of the sensing threshold may be computed and stored.

At decision block 332, a determination is made whether the episode is still being detected. If the episode is no longer being detected and has spontaneously terminated, the episode may be labeled as a non-sustained episode and this information is stored at block 334 for use in the episode profile.

If the episode is sustained at block 332, any scheduled therapy is delivered at block 336, and the therapies delivered and associated outcomes are stored. It is understood that more than one therapy may be delivered at block 332 if the episode is redetected after therapy delivery. Therapies may be repeated or a programmed sequence of progressively more aggressive therapies may be delivered until a therapy is successful and the episode is no longer redetected.

At block 340, the episode profile data established at blocks 332 through 336 are stored as an individual episode profile. Upon detecting a non-sustained episode at block 334 or successful termination of the episode, the complete episode profile is stored at block 340 with a date and time stamp. Storing the complete episode profile may include determining a total episode duration from time of detection at block 320 until episode termination, which may be the result of successful therapy or spontaneous termination. Additionally or alternatively, a total time duration from the initiating event detected at block 302 until episode termination may be stored as part of the complete individual episode profile.

Figure 7:
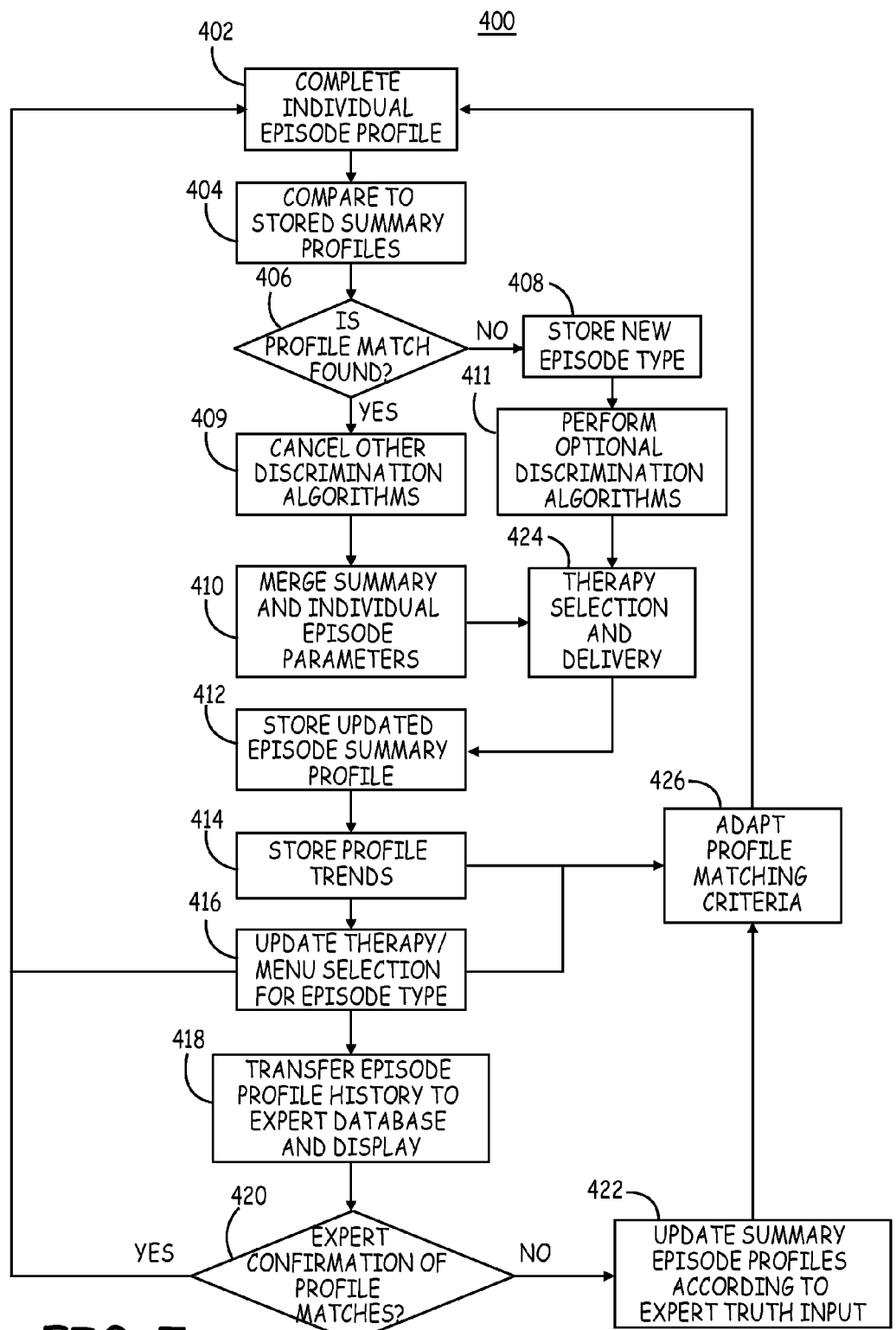
FIG. 7 is a flowchart of a method for updating an episode summary profile after obtaining a new individual episode profile.

FIG. 7 is a flowchart 400 of a method for updating an episode summary profile after obtaining a new individual episode profile. Upon completing an individual episode profile, as described above in conjunction with FIG. 6, the individual episode profile is compared to stored summary profiles at block 404. If there are no previously stored summary profiles, no profile match is found at decision block 406, and the individual profile is stored as a new episode type at block 408. It may be labeled using a selected nomenclature, which may be generic (e.g., "type 1") or may be more specific, e.g., "monomorphic fast VT type 1", or other selected labeling as desired. The individual profile is the summary profile for the new episode type.

If previous summary profiles are stored, the comparison performed at block 404 may involve a multi-step process in which the new individual episode is compared to the stored profiles until a match is found or until the individual profile has been compared to all summary profiles and no match is found. One process for finding a profile match is described below in conjunction with FIG. 8. If the new episode profile parameters fall outside an expected range of all parameters for the stored summary profiles, no match is found. The individual episode profile is stored as the summary profile for a new episode type at block 408. The new episode type is labeled appropriately, e.g. VT type n, VF type n, SVT type n, or the like, with a time and date stamp.

An optional block 411 may be included to allow additional discrimination algorithms to be performed when a new episode type is found. Reference is made, for example to U.S. Pat. No. 7,623,911 (Sarkar, et. al.), which generally describes a method for detecting atrial arrhythmias and discriminating atrial fibrillation (AF) and organized atrial tachycardia (OAT). The '911 reference is hereby incorporated herein by reference in its entirety. An algorithm may be performed to distinguish between different types of arrhythmia episodes and the result of the algorithm stored with the episode profile.

The result at block 406 may be used for selecting a therapy at block 424. As will be described in detail below, a therapy may be selected based on historical therapy data for a stored episode type. If no match is found at block 406 and a new episode type is stored at block 408, a default programmed menu of therapies may be selected and delivered at block 424. Delivered therapies, therapy delivery parameters, and therapy outcomes are used to complete the episode summary profile at block 412 for the new episode type.

If a profile match is found at block 406, any other discrimination algorithms currently executing or pending may be cancelled at block 409. Performing additional discrimination algorithms every time an episode is detected may increase the processing power burden and/or time for data collection. If a discrimination algorithm has been performed previously, at block 411, to distinctly classify the rhythm the first time the episode profile was stored, the discrimination algorithm need not be performed again. When an episode profile match is found, the known match result is used to automatically classify the rhythm. Additional discrimination algorithms, such as the AF/AOT discrimination algorithm described in the '911 patent, may be cancelled at block 409. Since patients sometimes experience the same type of episode repeatedly, matching the episode profile may allow the repeated episode type to be recognized using the profile parameters without performing more complex discrimination algorithms every time the episode occurs. In some embodiments, the additional discrimination algorithms may be performed for the first n times the episode type is found and the discrimination algorithm is disabled thereafter when the same episode type is found based on episode profile matching.

After finding a matching profile, the individual episode profile is merged with the matching summary profile at block 410. The matching summary episode profile may be used in therapy selection at block 424. A therapy is selected based on a preferred therapy stored for the episode type.

The process of merging the individual profile with the summary profile at block 410 is a multi-step process in which the profile parameters are averaged or combined in a method appropriate for each parameter. For example, some parameters may be an exact match and left unchanged, such as a classification, label, or categorical parameter value e.g., designating the episode as "polymorphic", "monomorphic", "sustained", "non-sustained", "accelerating", "not accelerating" etc. Such categorical parameters may be stored as digital high or low values (i.e. 1 or 0) which can be compared and designated as a match or no match. Typically, in order for the new individual profile to match the stored summary profile, these types of qualitative or categorical data stored in a digital format will exactly match, or at least a subset of these parameters may be required to exactly match.

Stored episode profile parameters relating to the pattern of counter adjustment may be qualitative, semi-quantitative or quantitative. For example, the counter adjustment pattern may be classified as increasing, intermittently increasing, intermittently increasing and decreasing, or other categories of behavior of the counter during the detection process. These classifications may be stored in digital code. In other embodiments, more quantitative or semi-quantitative values may be stored. For example, the number of cardiac cycles between the initiating event and detection that result in a counter increase, the number of cycles that result in no change in the counter, and the number of cycles that cause a decrease may be stored. When the counter is adjusted by values other than a value of one, e.g. the VT evidence counter described in the incorporated '615 application, the mean value and standard deviation of all increments and/or decrements applied to the VT evidence counter may be stored. These quantitative values may be averaged or combined in a weighted combination with summary profile values.

Other quantitative profile parameters, such as event interval metrics, mean matching score, and event amplitude metrics, may also be combined with corresponding summary profile parameter values using mathematical computations, such as averaging or using weighted combinations of summary parameter profile data and individual parameter profile data. When weighted combinations are used, the weighting coefficients chosen may depend on how many individual profiles have been merged to form the stored summary profile. If a single individual profile has been stored as the existing summary profile, the summary profile and the new individual profile parameter may be given equal weighting. The summary profile is given a greater weighting coefficient thereafter as new individual episode profiles are collected. In other embodiments, the individual parameter values of all the detected individual episodes of the same episode type are stored in an episode profile log and used with the new profile data to compute a new summary profile.

A representative morphology template from the individual profile may be averaged with a representative morphology template from the summary profile using a weighted combination of the summary profile and the individual profile (giving a heavier weighting coefficient to the summary profile morphology template). If the individual profile matches the summary profile with a very high correlation or matching score, e.g. at least 90 out of a possible score of 100, the summary profile morphology template may remain unchanged.

Therapy related parameters included in a summary profile may include, but are not limited to, a historical list of all successful therapies delivered for the episode type, the mean number of therapy attempts per episode, the type of therapy and/or therapy delivery parameters having the greatest frequency of success and a minimum or maximum therapy parameter value associated with therapy success.

After merging all of the profile parameters, the updated summary profile is stored at block 412, which may further include the selected therapies delivered at block 424 and associated outcomes. The updated summary profile will include a time/date stamp and may further include a total number of individual episodes detected contributing to the summary profile and time intervals between the individual episodes (i.e., frequency of episode type). The summary profile may include merged values for each parameter that is stored in an individual episode profile and may include other indices, status indicators or other overall summary metrics that summarize or represent a combination of profile parameter values in a clinically meaningful way. For example a status may indicate that an episode type represented by the summary profile is a fast, deteriorating potentially lethal VT/VF that is occurring with increasing frequency. Another summary profile status may indicate the episode type is a slow, stable intermittent VT/VF that has been known to spontaneously terminate.

At block 414, a trend of the profile data is determined and stored. The latest individual profile may be compared to the summary profile at the time of the current episode detection or to a previous individual profile to determine a profile trend. Alternatively, the updated summary profile may be compared to any previous summary profile or individual profile. Trends in the episode profile can be useful to a clinician in tracking the physiological condition of the patient. For example trends indicating a counter adjustment pattern is more rapidly increasing to a detection threshold, a trend of increasing rate acceleration, a trend of more aggressive therapies being required to successfully terminate the episode type, a trend of shorter time intervals between the same episode types (increasing frequency of the episode type), a worsening trend in the mean morphology score, or other profile trends may indicate a worsening condition of the patient, a need to check the ICD system and programmed operating parameters, or other indicators useful to a clinician in managing the patient.

In order to determine profile trends, a distance metric may be computed for determining how closely (or how distantly) a recent individual or summary profile matches a previous individual or summary profile. The distance metric may be computed using differences between each of the profile parameters. The distance metric may be stored at block 414 as an indicator of a trend in the episode type.

At block 416, a programmed therapy or menu of therapies to be delivered upon detecting the episode type is updated using the updated summary profile. The programmed therapy or menu for responding to the episode type the next time it is detected may be adjusted based on therapy outcomes stored in the updated summary profile. Adjustments to a programmed therapy or menu of therapies are based on the summary profile therapy data. The summary profile therapy data may include therapies/therapy parameters that have demonstrated the greatest success, the greatest success with the least battery charge consumed, the shortest total time to episode termination, the least aggressive therapy known to be successful or any combination thereof. Therapy/menu adjustments performed at block 416 may include removing a therapy or adjusting a therapy parameter known to result in a failure to terminate the arrhythmia episode. Thereafter, the process returns to block 402 to await the next complete individual episode profile.

At any time, the ICD may be interrogated to retrieve episode profile data. At block 418, the episode profile data is transferred to an expert database, a clinician computer, programmer, networked patient monitoring system or other external data destination used for patient management that allows an expert to view the profile data. Both newly acquired profile data and historical profile data retrieved in a previous data transfer may be displayed in detailed and summary formats. The expert may view newly detected episodes and corresponding summary profile matches (if any). The expert may view available summary episode profiles along with a sample EGM strip and/or profile data of each detected individual episode and verify that any match found by the IMD between an individual episode profile and a summary profile (or the finding of no match) is correct.

The expert may be prompted to provide a truth input for verifying a match (or no match) and can indicate a correct match with a different summary profile if an automatically-determined match is incorrect. If all episode matches are correct at block 420, no changes are made and the process returns to block 402 to wait for the next complete individual episode profile.

If any match is incorrect, the expert provides the appropriate truth input indicating a correct match with a summary profile (or no match), and any summary episode profiles affected by the expert truth input are updated accordingly at block 422. Additionally at block 422, the profile trends and therapy menu programmed for a particular episode type may be updated in response to the updated summary profile(s). The process then returns to block 402 to await the next complete individual episode profile.

The process represented by flow chart 400 may be a self-learning, self-adaptive algorithm. For example, in response to expert truth input, profile matching criteria may be adjusted at block 426 such that profile matching that previously resulted in an incorrect result based on expert truth input would now result in the same result provided by the expert.

When expert truth input is not available, profile matching criteria may still be adapted and "learned" by responding to profile trends (block 414) and therapy information (block 416). Matching criteria, for example matching ranges for a particular profile parameter, may be adjusted based on trends in the profile parameters such that an predicted range of the parameter is defined on which future profile matching is based. If a profile trend is very stable, relatively narrow or stringent matching criteria may be defined. If the trend is more variable, relatively wider matching criteria may be defined.

If a therapy known to treat the episode type with a high frequency of success fails, the profile match may be flagged as questionable. The episode resulting in a questionable match may be stored as a possible new episode type. The possible new episode type may be either confirmed or removed based on future episode profile matching results. As such, the accumulation of episode profile data is dynamic with new episode summary profiles being added or removed as appropriate and episode matching criteria being dynamically adjusted based on therapy results, profile trends, and/or expert truth input.

Figure 8:
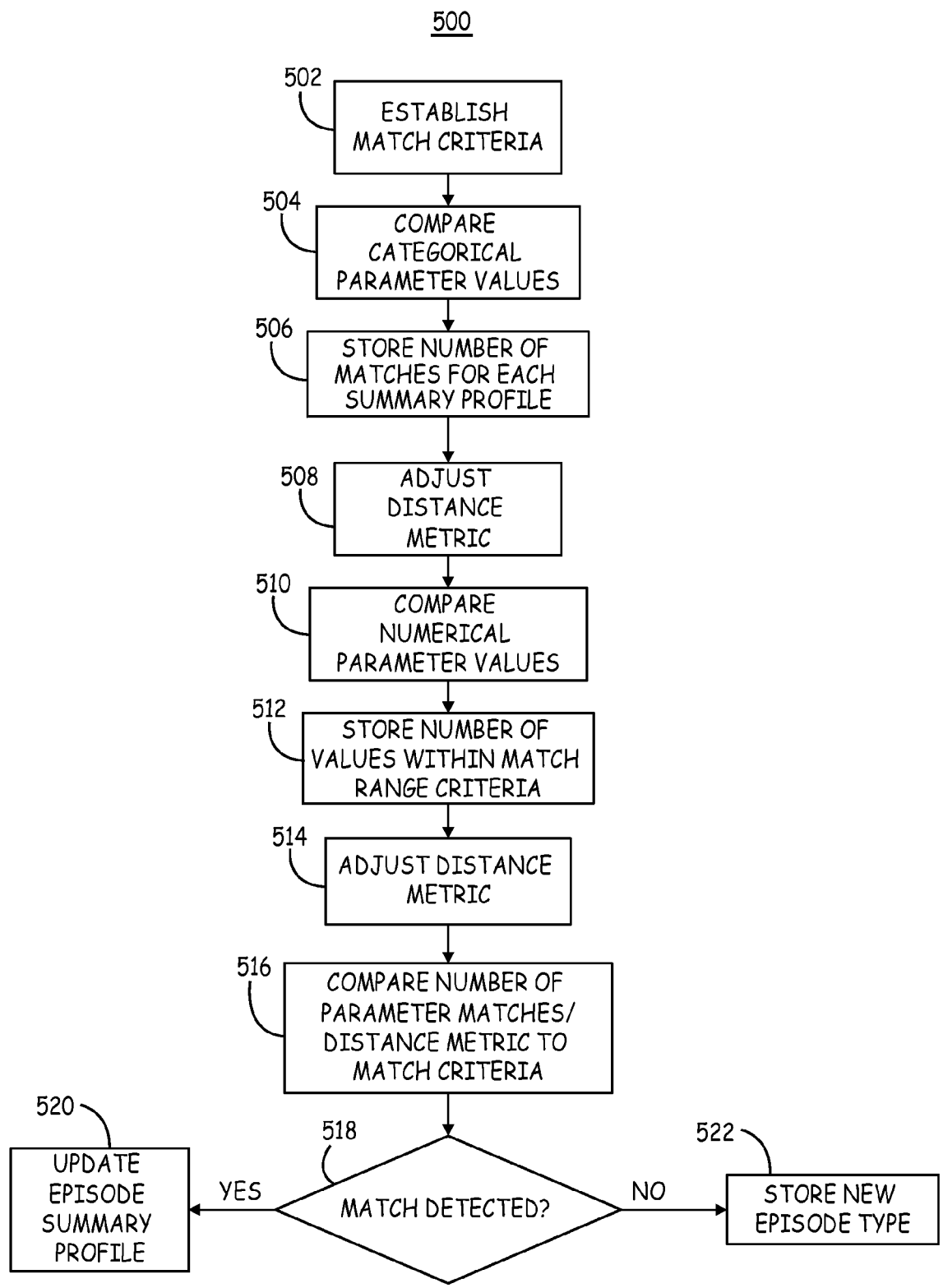
FIG. 8 is a flowchart of a method for comparing an individual episode profile to an episode summary profile for use in classifying a detected episode.

FIG. 8 is a flowchart 500 of a method for comparing an individual episode profile to an episode summary profile for use in classifying a detected episode. A correlation between a detected episode and previously stored episode profiles is determined to allow a newly detected episode to be grouped or classified with previously detected episodes having a high correlation of episode profile parameters. It is recognized that numerous methods may be used for computing a correlation between a new and previously stored episode profile.

In the illustrative example of FIG. 8, match criteria are established at block 502. Match criteria may include initial default parameter ranges or may be tailored according to clinician preferences, patient need, or historical clinical data. The match criteria may include criteria defining required correlation between individual episode profile parameter values as well as overall matching criteria for defining a profile match, as described in greater detail below. The match criteria may be established at block 502 during a self-adapting, "learning process" as described above. The match criteria may be adjusted over time in response to expert truth input, profile trends, and therapy outcomes.

At block 504, any categorical parameter values of a newly detected episode are compared to corresponding categorical parameter values for all stored summary profiles. The number of parameter value matches found for each of the summary profiles is stored at block 506. In some cases, categorical parameter values may be stored as a numerical value, such as category 0, 1, and so on, depending on the number of categories. For example a categorical parameter value may designate the rhythm as polymorphic or monomorphic, another parameter value may designate the rhythm as accelerating or non-accelerating, another parameter value may indicated the rhythm as being sustained or non-sustained, and yet another parameter value may indicate as continuously increasing counter pattern, intermittently increasing counter pattern, or other wise. For each of the summary profiles, the number of categorical parameters matching the new individual episode profile is stored at block 506.

A distance metric is adjusted at block 508. The distance metric may be a counter for counting the number of exact or highly correlated matches between summary profile and individual profile parameters. Alternatively, the distance metric may sum the numerical differences between each individual profile parameter value and its corresponding summary profile parameter value. A distance metric may be computed for all stored summary profiles, only the summary profiles found to have at least one categorical match, or only a summary profile identified to have an exact match of all categorical profiles. An exact match between all categorical profile values would result in a distance metric of 0 in one embodiment indicating an exact or highly correlated match. Alternatively, a matching metric may be used in place of a distance metric that will have a high value when a high correlation exists.

At block 510, quantitative parameter values of the individual profile are compared to corresponding summary parameter values. Quantitative profile parameter values may be compared between the individual profile and all summary profiles available, or only those having a low or zero distance metric value after comparing categorical parameter values.

Each quantitative, numerical parameter value of the individual profile may be compared to a respective summary parameter value to determine if the individual parameter value falls within an established matching range. A matching range may be defined for each parameter value based on default values, clinical data, individual patient history or the like. Alternatively, a correlation between all numerical parameter values of the individual profile and all numerical parameter values of the summary profile may be computed. The correlation coefficient and/or the number of numerical parameter values falling within the parameter's established matching range of the respective summary profile parameter value are stored at block 512.

The distance metric is adjusted at block 514. The distance metric may be increased for every parameter value that falls outside a matching range or has a low correlation relative to a summary parameter value. The distance metric may be decreased for every parameter value that is within a matching range or has a high correlation with a summary parameter value. In some embodiments, the distance metric may be increased by a difference between each numerical parameter value, after applying desired weighting coefficients or normalizing factors. In this embodiment, the distance metric may be increased for all parameter values not having an exact match between the individual and summary profile parameters, but will be increased by a smaller amount when the difference (or distance) between parameter values is smaller. An exact match may cause the distance metric to remain unchanged or decrease.

At block 516, overall matching criteria are applied to detect a match between a summary profile and an individual profile. The overall matching criteria may require a minimum number of parameter matches (i.e. the parameter value falls within an established parameter-specific matching range of the summary profile parameter value). The overall matching criteria may additionally apply threshold limits to a distance metric, match metric and/or overall correlation coefficient.

At block 518, the summary profile resulting in the closest match, e.g. lowest distance metric, greatest number of parameter matches, or highest correlation coefficient, is found as a profile match. The matching summary profile is updated at block 520 using the individual profile episode data. If no profile match is found, i.e. no profile comparison meets the required match criteria, the episode is stored as a new summary episode at block 522.

Figure 9:
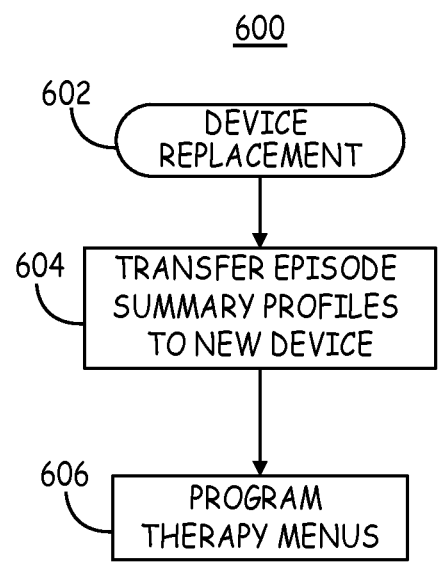
FIG. 9 is a flowchart of a method for transferring episode summary profile data to a replacement IMD.

FIG. 9 is a flow chart 600 of a method for transferring episode summary profile data to a new device upon device replacement. Periodically, an IMD may be replaced for any of a number of reasons. The battery of an implanted device may be approaching or have reached end-of-life. A newer device may be available with features desirable for the patient. The patient's condition may have changed requiring a device with different capabilities than a currently implanted device.

When a device replacement procedure is taking place, as indicated at block 602, the episode summary profile data stored in the device being explanted can be transferred to the new device being implanted at block 604. This transfer may be made by first uploading the profile data to an external programmer or database then downloading the profile data from the external programmer or database to the replacement IMD. If IMDs are enabled for direct communication with each other, the transfer may be made directly.

At block 606, the initial settings for arrhythmia therapies in the replacement device may be programmed according to the transferred profile data. This process may be automatic based on the episode data. For each episode profile that the patient has experienced, a therapy or menu of therapies may be set based on the episode profile history. A default therapy may be based on the most common episode experienced by the patient and the therapy parameters found to successfully terminate that episode type.

Thus, a medical device and associated method for establishing and using arrhythmia episode profiles have been presented in the foregoing description with reference to specific embodiments. It is appreciated that various modifications to the referenced embodiments may be made without departing from the scope of the disclosure as set forth in the following claims.

The invention claimed is:

1. A method, comprising:
sensing a cardiac signal;
initiating an arrhythmia episode detection process in response to the cardiac signal by enabling an arrhythmia detection counter to be adjusted during the detection process;
accumulating data relating to cardiac events during the detection process;
establishing an arrhythmia episode profile using the accumulated data; and
discriminating between arrhythmia episode types in response to the established profile, wherein accumulating data comprises determining a pattern of the adjustment of the counter during the detection process, wherein determining the pattern of the adjustment comprises storing a notation on each cardiac cycle during the detection process indicating a direction of a counter value change as being one of up, down and no change.

2. The method of claim 1, wherein establishing the episode profile comprises storing a plurality of categorical and quantitative episode parameters using the accumulated data.

3. The method of claim 1, further comprising:
determining a correlation between a previously stored summary profile and the established episode profile; and
classifying the established episode profile in response to the correlation.

4. The method of claim 3, wherein the established episode profile comprises a plurality of profile parameters, and wherein determining the correlation comprises:
determining a correlation between each of the plurality of profile parameters of the established episode profile to a respective profile parameter of the summary profile; and
computing a distance between the established profile and the summary profile in response to the determined correlations of the plurality of profile parameters.

5. The method of claim 4, further comprising updating the stored summary profile in response to the correlation between the previously stored summary profile and the established episode profile.

6. The method of claim 5, further comprising:
storing the summary profile in an implantable medical device; and
transferring the summary profile to a replacement implantable medical device.

7. The method of claim 4, further comprising:
receiving expert truth input indicating a correct match between an individual profile and a previously stored summary profile; and
updating the stored summary profile in response to the expert truth input.

8. The method of claim 4, further comprising selecting a therapy in response to the correlation.

9. The method of claim 8, further comprising updating the established episode profile in response to the selected therapy and an outcome of the selected therapy.

10. The method of claim 9, further comprising:
updating the summary profile in response to the updated established profile; and
adjusting a programmed menu of therapies in response to the updated summary profile.

11. The method of claim 8, further comprising determining a profile trend in response to the updated summary profile.

12. The method of claim 4, further comprising cancelling a discrimination algorithm in response to the correlation.

13. The method of claim 1, further comprising deriving from the stored notations a summary metric indicating the pattern of adjustment.

14. A medical device, comprising:
a plurality of electrodes sensing a cardiac signal; and
a processor configured to initiate an arrhythmia episode detection process in response to the cardiac signal by enabling an arrhythmia detection counter to be adjusted during the detection process, accumulate data relating to cardiac events during the detection process, establish an arrhythmia episode profile using the accumulated data, and discriminate between arrhythmia episode types in response to the established profile, wherein accumulating data comprises determining a pattern of the adjustment of the counter during the detection process, wherein determining the pattern of the adjustment of the counter comprises storing a notation on each cardiac cycle during the detection process indicating a direction of a counter value change as being one of up, down and no change.

15. The device of claim 14, wherein establishing the episode profile comprises storing a plurality of categorical and quantitative episode parameters using the accumulated data.

16. The device of claim 14, wherein the processor is further configured to determine a correlation between a previously stored summary profile and the established episode profile, and classify the established episode profile in response to the correlation.

17. The device of claim 16, wherein the established episode profile comprises a plurality of profile parameters, and wherein the processor is further configured to determine a correlation between each of the plurality of profile parameters of the established episode profile to a respective profile parameter of the summary profile and compute a distance between the established profile and the summary profile in response to the determined correlations of the plurality of profile parameters.

18. The device of claim 17, wherein the processor is further configured to update the stored summary profile in response to the correlation between the previously stored summary profile and the established episode profile.

19. The device of claim 18, further comprising a telemetry circuit to transfer the summary profile to a replacement implantable medical device.

20. The device of claim 17 further comprising a user interface to receive expert truth input indicating a correct match between an individual profile and a previously stored summary profile, wherein the processor is further configured to update the stored summary profile in response to the expert truth input.

21. The device of claim 17, further comprising a therapy delivery module, wherein the processor is configured to select a therapy in response to the correlation.

22. The device of claim 21, wherein the processor is further configured to update the established episode profile in response to the selected therapy and an outcome of the selected therapy.

23. The device of claim 22, wherein the processor is further configured to update the summary profile in response to the updated established profile and adjust a programmed menu of therapies in response to the updated summary profile.

24. The device of claim 22, wherein the processor is further configured to determine a profile trend in response to the updated summary profile.

25. The device of claim 17, wherein the processor is further configured to cancel a discrimination algorithm in response to the correlation.

26. A non-transitory computer-readable medium storing a set of instructions which cause a processor of a medical device to:
- sense a cardiac signal;
- initiate an arrhythmia episode detection process in response to the cardiac signal by enabling an arrhythmia detection counter to be adjusted during the detection process;
- accumulate data relating to cardiac events during the detection process;
- establish an arrhythmia episode profile using the accumulated data; and
- discriminate between arrhythmia episode types in response to the established profile, wherein accumulating data comprises determining a pattern of the adjustment of the counter during the detection process, wherein determining the pattern of the adjustment comprises storing a notation on each cardiac cycle during the detection process indicating a direction of a counter value change as being one of up, down and no change.

* * * * *